Figure 1:
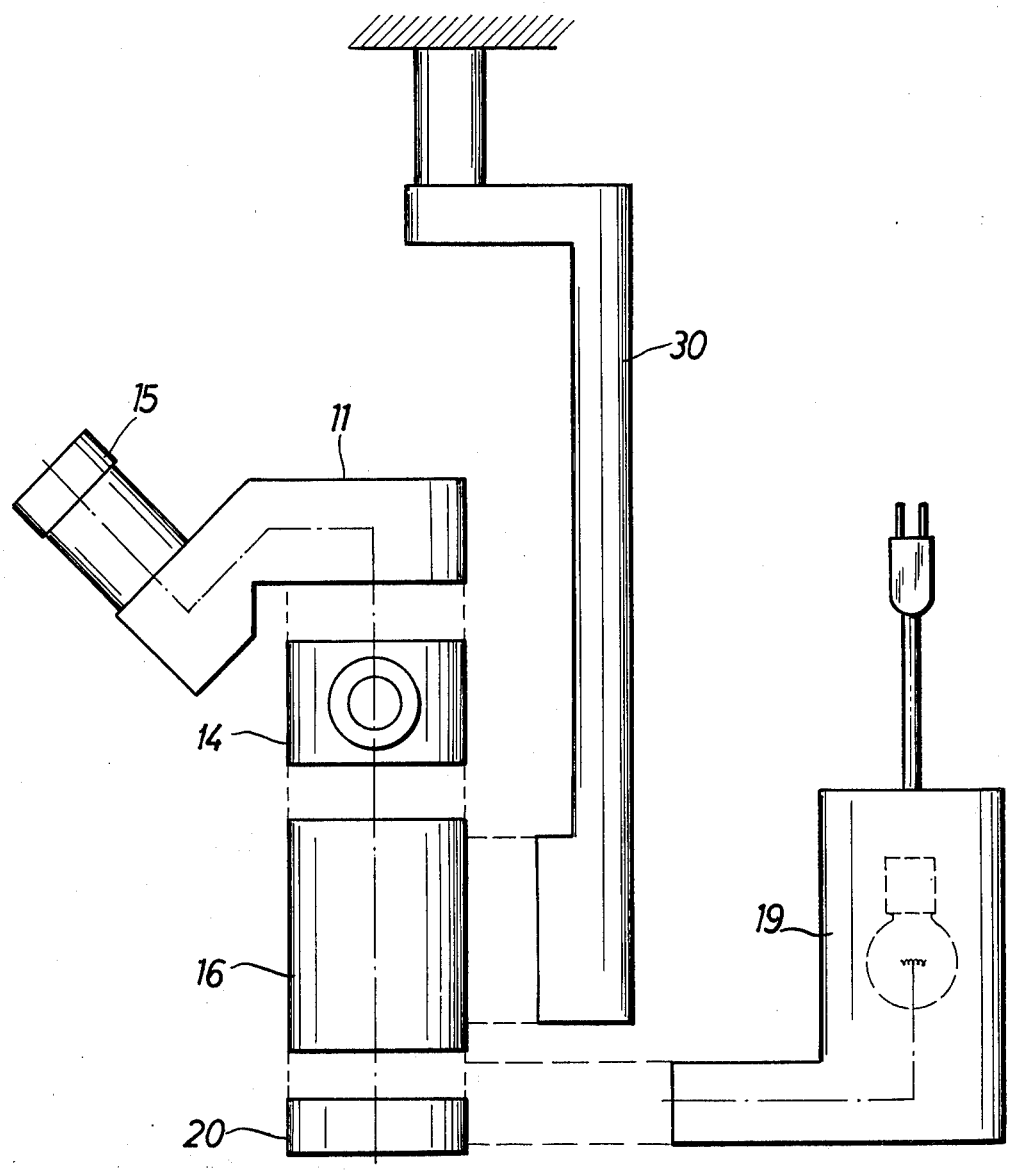

United States Patent [19]

Klein

[11] 4,035,057

[45] July 12, 1977

[54] FLOOR OR CEILING SUPPORT MOUNTED MICROSCOPE FOR MICROSURGICAL APPLICATIONS

[75] Inventor: Friedrich Klein, Wedel, Holstein, Germany

[73] Assignee: J.D. Möller Optische Werke GmbH, Wedel, Holstein, Germany

[21] Appl. No.: 597,992

[22] Filed: July 22, 1975

[30] Foreign Application Priority Data

Aug. 27, 1974 Germany .......................... 2440958

[51] Int. Cl.² .................. G02B 23/16; G02B 21/18
[52] U.S. Cl. .................................. 350/85; 350/19; 350/33
[58] Field of Search ............................. 350/82–85, 350/19, 33–36; 351/7

[56] References Cited

U.S. PATENT DOCUMENTS

| | | | |
|---|---|---|---|
| 2,967,458 | 1/1961 | Stone | 350/85 X |
| 3,372,616 | 3/1968 | Morrison | 351/7 X |
| 3,656,829 | 4/1972 | Wilms | 350/33 |
| 3,776,614 | 12/1973 | Kloots et al. | 350/85 |
| 3,868,171 | 2/1975 | Hoppl | 350/85 |

FOREIGN PATENT DOCUMENTS

1,217,099  5/1966  Germany ........................... 350/33

*Primary Examiner*—David H. Rubin
*Attorney, Agent, or Firm*—Toren, McGeady and Stanger

[57] ABSTRACT

A floor or ceiling mounted microscope for microsurgery with various accessories wherein the microscope is rotatably journalled in a suspension mounting in a manner so that the pivot axis of the microscope coincides with the axis of the beam splitter. The accessories may either be rigidly secured to the suspension mounting, or be rotatable together with the microscope.

3 Claims, 3 Drawing Figures

FLOOR OR CEILING SUPPORT MOUNTED MICROSCOPE FOR MICROSURGICAL APPLICATIONS

The present invention relates to a floor or ceiling support mounted microscope for microsurgical applications which includes a viewing unit, an eyepiece, an objective, a magnification changer, a beam splitter mounted intermediate the viewing unit and the magnification changer, and, optionally, a photographic camera, a movie camera, a television camera and/or a dual viewer unit.

High quality microscopes for microsurgical applications include a variety of modular units that may be interchangeably assembled and which by their different properties and performance allow the ready adaptation to the pecularities of different microsurgical requirements.

The base model of such a microscope for microsurgery includes a viewing unit with eyepieces and an objective. The viewing unit is a binocular afocal system. The viewing unit and the objective are interconnected by an element which simultaneously serves as a mounting or a support for the microscope and allows to perform further functions such as focussing by means of a traveling carriage guide or the tilting of the microscope about an axis within a fork type bracket.

Viewing units with different viewing angles are available, such as for straight-line viewing, for viewing at an angle of 45° and the like. The eyepieces are generally exchangeable so as to further broaden the possibilities of varying the magnification.

Objectives may be supplied at various focal lengths, ranging generally from 125 to 500 mms, and the objectives will be selected according to the working distance required.

The overall magnification of the microscope is dependent upon the viewing unit, the eyepiece and the selected objective. For modifying or respectively enlarging the available range of microscope magnification there may furthermore be employed a magnification changer that is mounted intermediate the viewing unit and the objective. Magnification changers are generally afocal systems in the form of step-by-step magnification changers, preferably Galileo systems mounted on indexing drums, or in the form of continuously variable zoom lens magnification changers.

Further accessories for these microscopes are beam splitters that are mounted intermediate the viewing unit and the magnification changer and allow by means of additional objectives to extend the microscope ray path likewise to photographic, movie and television cameras or dual viewer units.

The illumination unit generally consists of lamps some of which are adjustable and illuminate the field of view laterally at small angles. These lamps are mounted behind the objective and illuminate the object approximately in a direction coaxial with the objective.

By the increased usage of television, movie and photographic cameras the handling of such microscopes becomes more and more cumbersome. In the above described design the center of gravity of such additional apparatus cannot be made to coincide with the horizontal pivot axis of the microscope, or rather intricate swiveling means would be required.

For the usage during operations, the microscopes of the above described type are mounted on floor or ceiling supports. Most of these supports provide for motor-driven height adjustment whereby this height adjustment might also be used for focussing the microscope when the latter is used in a vertical alignment. When the microscope is tilted, however, focussing must be performed by means of the swiveling carriage of the mounting. Toward this end, this carriage generally includes manual or motor-driven adjustment means.

It is now the main object of the present invention to provide a microscope that is suitable for microsurgery in which additional accessories such as photographic cameras, movie cameras, television cameras or dual viewer units do not interfere with the activities of the operating surgeon when swiveling the microscope.

For achieving this object, there is now proposed, in accordance with the present invention, a microscope which is rotatably journalled in a suspension mounting in a manner so that the pivot axis of the microscope coincides with the beam splitter exit axis.

The invention furthermore relates to a microscope with a photographic camera, a movie camera, a television camera and/or a dual viewer unit whereby the photographic camera, the movie camera, the television camera and/or the dual viewer unit may either by rigidly secured to the suspension mounting or be mounted on the suspension mounting so as to be rotatable together with the microscope.

A microscope arranged in this manner has the important advantage that the microscope may be moved without the accessories attached thereto interfering with the activities of the operating surgeon. Additionally, the inventive arrangement of the microscope in the suspension mounting has the advantageous effect that no large masses and weights need be moved.

By arranging the pivot axis of the microscope so as to coincide with the beam splitter exit axis the following arrangements are possible:

According to one embodiment, the camera or the accessory unit provided is rotated jointly together with the microscope. In another embodiment the camera or accessory unit is maintained in a predetermined position with respect to the suspension mounting. In the latter case, when changing the tilt angle, merely the microscope is being tilted so that considerable weights and masses need no longer be moved. This will, however, result in a rotation of image which may readily be eliminated by conventional means such as erecting prisms, rotating the camera or the like and s.o.

Figure 2:
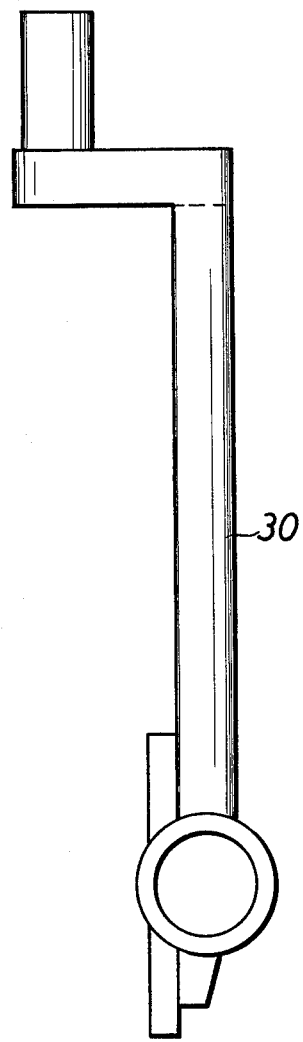
Figure 3:
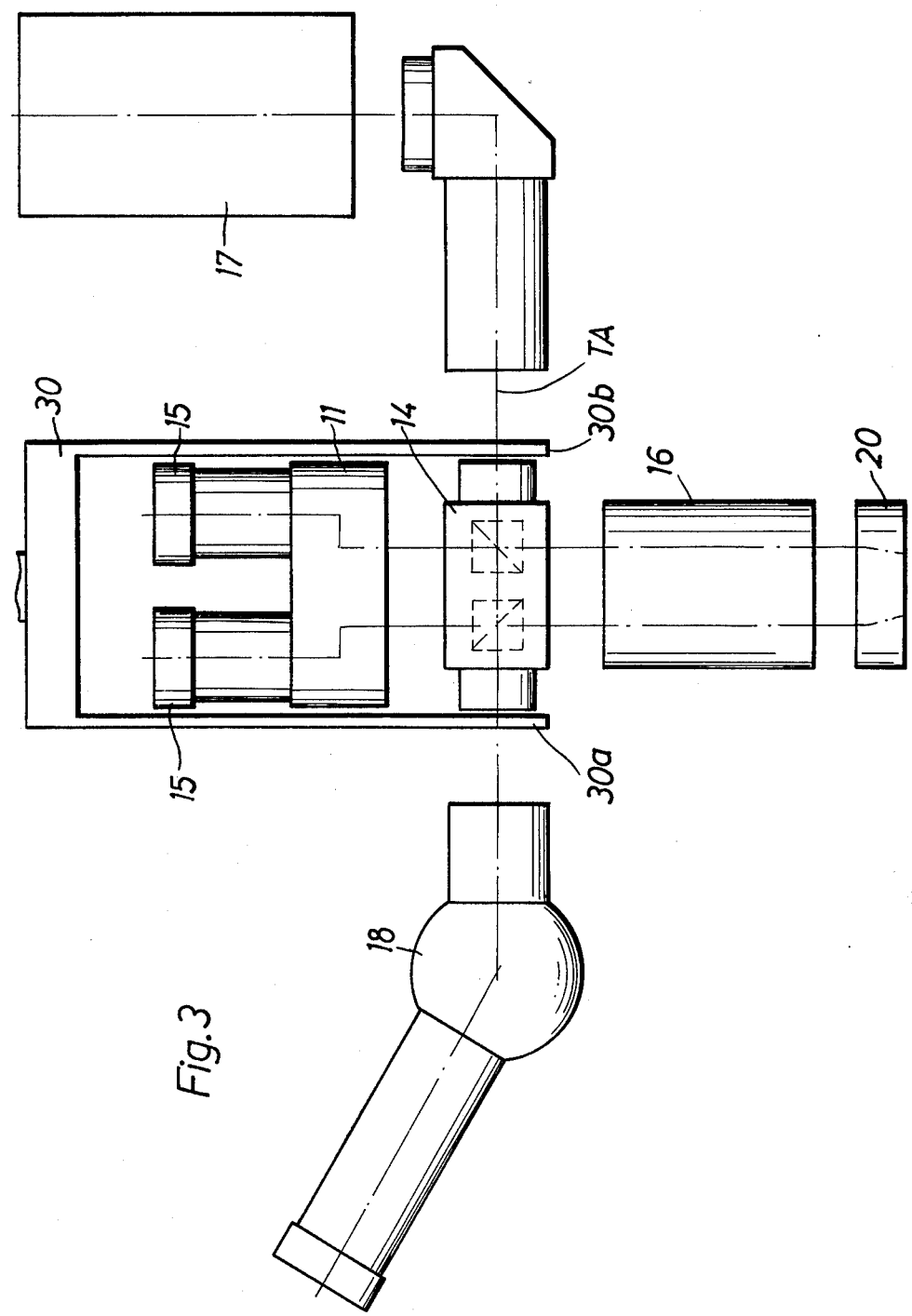

An embodiment of the microscope of the present invention is shown in the appended drawing wherein FIG. 1 is a schematical lateral elevational view of a microscope with its various assemblies;

FIG. 2 is a lateral elevational view of the microscope support with coaxially arranged pivot and carriage adjustment means; and FIG. 3 is a schematical front elevational view of a microscope with dual viewer unit and a camera, illustrating the various assemblies.

Referring to the embodiment of a microscope in accordance with the present invention shown in FIGS. 1–3, the microscope is designated by the reference 10. The microscope includes a housing for receiving a viewing unit 11 with eyepieces 15, and an objective 20. The overall arrangement is mounted in a suspension mounting 30. This suspension mounting 30 may form part of a floor or ceiling support not shown in the drawings. The mounting 30 holds the microscope and in the embodiment according to FIG. 2 also allows to tilt the microscope. The viewing unit 11 may provide any of several different viewing directions, i.e. straight-through viewing, viewing at an angle of 45° and the like. The objectives may have as desired any of various focal lengths. The overall magnification of the microscope is predetermined by the viewing unit 11, the eyepiece 15 and the objective 20. For enlarging or modifying the microscope magnification may be provided a magnification changer 16 that is mounted intermediate the viewing unit 11 and the objective 20.

As may be seen from the embodiment of FIGS. 1 and 3, the microscope housing may receive further components such as a beam splitter 14 mounted intermediate the viewing unit 11 and the magnification changer 16. A photographic camera, a movie camera or a television camera indicated generally by the reference 17, and a dual viewer unit 18 may likewise be provided. The camera 17 and the dual viewer unit 18 participate in the viewing path of the microscope. The reference numeral 19 designates an illumination unit.

As shown in FIG. 3, the microscope 10 is journalled in the suspension mounting 30 in a manner so that the microscope pivot axis coincides with the beam splitter exit axis TA. The camera or other accessory 17 and/or the dual viewer unit 18 are then rigidly secured to the spars 30a, 30b of the suspension mounting 30. These points of attachment may either be located in the vicinity of the microscope pivot axis or at points along the spars 30a, 30b that are above the microscope pivot axis so that the accessories 17, 18 will not obstruct the operating surgeon when swiveling the microscope. Any resulting rotation of image may be eliminated by conventional means such as erecting prisms or the like.

It is likewise possible to arrange the accessories 17, 18 at the suspension mounting of the microscope 10 in a manner so that these accessories 17, 18 may be rotated together with the microscope 10.

In the above described embodiment the microscope for microsurgical applications preferably includes an objective 20 of variable intercept length, this, however, not being required.

What is claimed is:

1. A microscope assembly for microsurgical applications adapted for mounting from a support and to have accessory units mounted in cooperative relationship therewith, said assembly comprising a microscope including a viewing unit, an eyepiece, an objective and a magnification changer, said microscope being arranged to define a main viewing path extending in a given direction along the optical axis of said objective, suspension mounting means defining a pivot axis extending perpendicularly to said given direction pivotally mounting said microscope from said support to enable rotative change of said viewing direction around said pivot axis, a beam splitter mounted intermediate said viewing unit and said magnification changer defining an auxiliary viewing path for said accessory units, said auxiliary viewing path extending at least over a portion of its length perpendicularly to said given direction of said main viewing path and coincident with said pivot axis of said microscope, said pivot axis defined by said suspension mounting means having an open central portion to define therethrough the coincident portion of said auxiliary viewing path, and at least one accessory unit mounted to receive an image identical to the image received by said microscope along said auxiliary viewing path.

2. A microscope assembly according to claim 1 wherein said at least one accessory unit is rigidly secured to said suspension mounting means.

3. A microscope assembly according to claim 1 wherein said at least one accessory unit is mounted on said suspension mounting means in a manner to be rotatable together with said microscope.

* * * * *